United States Patent [19]

Lee et al.

[11] Patent Number: 5,006,068

[45] Date of Patent: Apr. 9, 1991

[54] DENTAL IMPLANT

[76] Inventors: Chong Jin Lee, 291-1, Namgajwa-Dong, Seodaemun-gu; Dong Seok Kim, 5-5, 852-744, Mia 7-Dong, Dobong-gu, both of Seoul, Rep. of Korea

[21] Appl. No.: 574,486

[22] Filed: Aug. 28, 1990

[30] Foreign Application Priority Data

Jul. 14, 1990 [KR] Rep. of Korea ............... 90-10696

[51] Int. Cl.$^5$ ................................................ A61C 8/00
[52] U.S. Cl. .................................... 433/169; 433/173
[58] Field of Search ............... 433/169, 173, 174, 175, 433/176, 201.1

[56] References Cited

U.S. PATENT DOCUMENTS

| | | | |
|---|---|---|---|
| 3,722,094 | 3/1973 | Rivoir | 433/169 |
| 4,552,532 | 11/1985 | Mozsary | 433/174 |
| 4,626,214 | 12/1986 | Artal | 433/169 |
| 4,713,003 | 12/1987 | Symington et al. | 433/173 |
| 4,881,897 | 11/1989 | Franek et al. | 433/169 |

Primary Examiner—John J. Wilson
Attorney, Agent, or Firm—Ladas & Parry

[57] ABSTRACT

A dental implant comprising a foundation shaft having a head spaced apart from a supporting ring with a carrier body slidably positioned therebetween is disclosed. The movement of the carrier body is limited to the distance between the head and the supporting ring less the length of the foundation shaft occupied by the carrier body. The second end of the foundation shaft includes a securing means for fixing the dental implant to the jaw bone. An aperture is formed in an elongated body for receiving a resilient force dampening means which maintains contact of the carrier body with the head in the absence of masticatory movement of the jaw and also resists axial movement of the tooth assembly generated by masticatory movement of the jaw thereby cushioning the masticatory forces received by the foundation shaft during use. A connecting means secures the elongated body to the carrier body such that upon the attachement of the artificial tooth to the elongated body-carrier body, a tooth assembly is defined. Means are disclosed for attaching an artificial tooth to the elongated body.

14 Claims, 2 Drawing Sheets

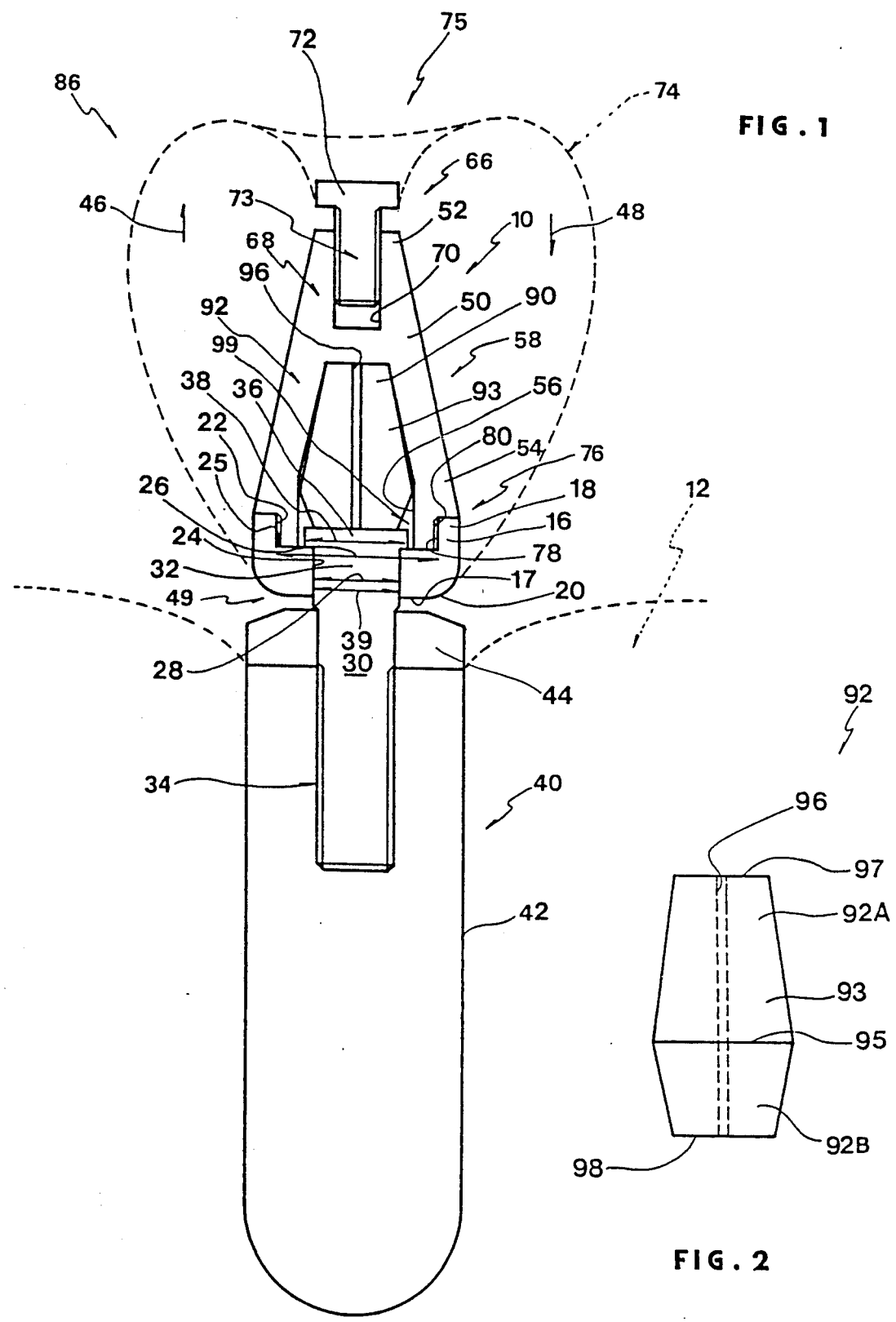

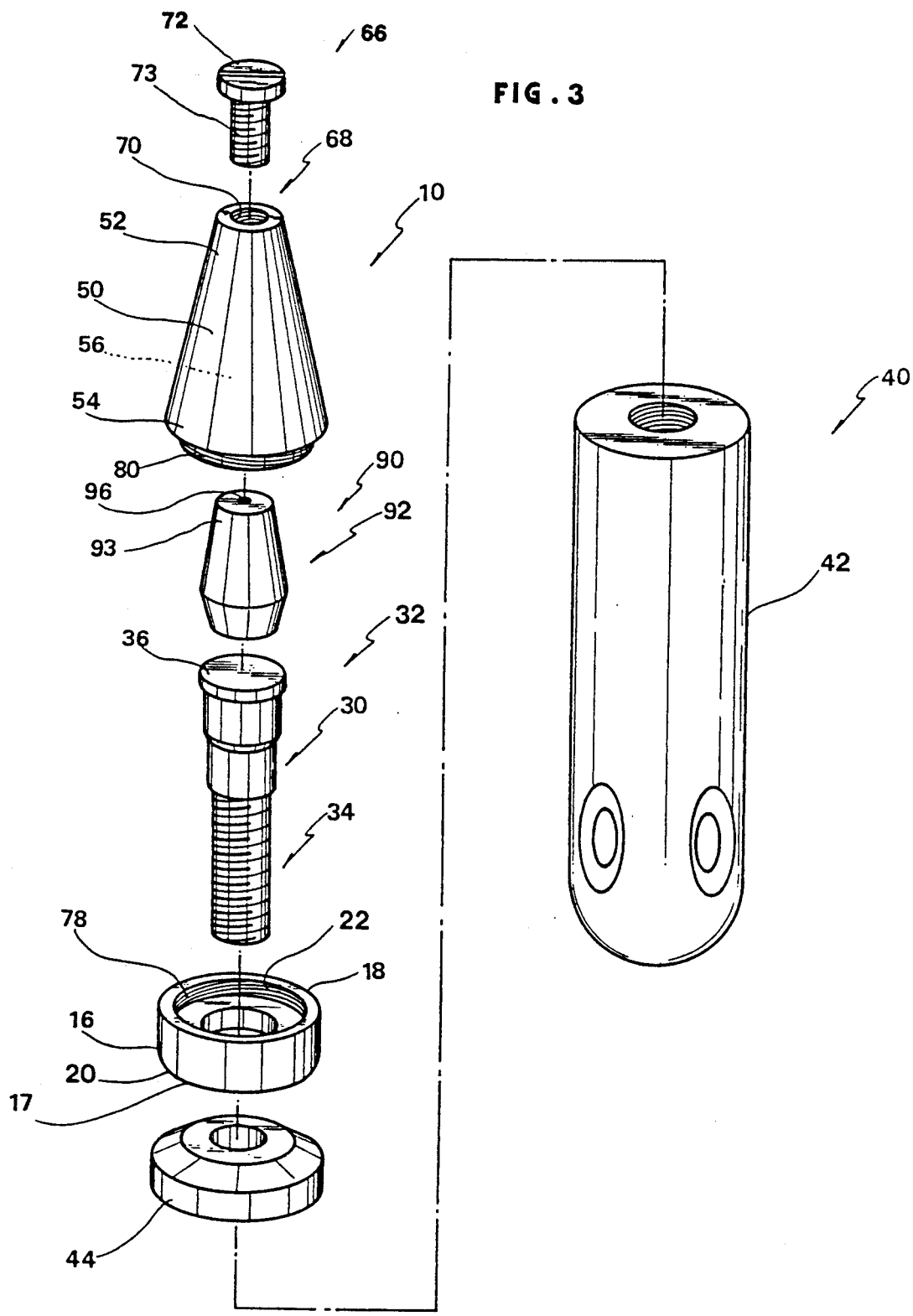

DENTAL IMPLANT

BACKGROUND OF THE INVENTION

Field of the Invention

This invention relates to a dental implant system utilizing a force dampening means, and more particularly, to a resilient force dampening means having a bi-frustum shaped silicon rubber body for positioning into a frustum shaped aperture in order to absorb the forces generated during chewing.

There is a need to provide an improved dental implant which better simulates the reaction of a natural tooth upon receiving the forces associated with chewing. Recent implant systems have been designed to mimic the natural tooth's ability to deal with the forces encountered in chewing in both tooth movement and tooth shock absorbing characteristics.

One such system, U.S. Pat. No. 4,552,532, utilizes a root secured to the jaw bone, a post supported to the root with a crown connected thereto. A member is provided for cushioning the forces applied to the crown. A stop is also included to limit the movement between the crown and the root. A cushioning member surrounds the portion of the post positioned in the root and extends horizontally across the interface between the crown-upper post and the root-lower post. The cushioning members may be composed of silicon rubber or TEFLON.

Another system, U.S. Pat. No. 4,626,214, utilizes a first body, having an axial hole, secured in the jaw bone, into which an O-ring and the lower portion of a second body are positioned. The upper portion of the second body holds the crown. At the interface between the bottom of the crown and the top of the first body, a second O-ring is positioned. The O-rings enable a slight axial dampening movement to mimic a natural tooth.

However, such implant systems are relatively complex and utilize more than one force dampening means to simulate the action of a natural tooth. Other implant systems fail to sufficiently absorb the axial forces, impacts and the like generated during chewing. Thus, such systems may feel unnatural to the person using such prior art dental implant systems.

An object of the present invention is to provide a dental implant which utilizes a single force dampening means to attenuate the forces received by the implant during chewing.

A further object of the present invention is to provide a dental implant which utilizes a bi-frustum shaped silicon rubber body with an opening formed therethrough which is positioned into a frustum shaped aperture.

A further object of the present invention is to provide a dental implant which simulates the force dampening effect of a natural tooth.

A further object of the present invention is to provide a dental implant having a single force dampening means which can be easily replaced.

A further object of the present invention is to provide a dental implant which is relatively inexpensive to manufacture.

The preceding objects should be construed as merely presenting a few of the more pertinent features and applications of the invention. Many other beneficial results can be obtained by applying the disclosed invention in a different manner or modifying the invention within the scope of the disclosure.

Accordingly, other objects and a fuller understanding of the invention may be had by referring to both the summary of the invention and the detailed description, below, which describe the preferred embodiment in addition to the scope of the invention defined by the claims considered in conjunction with the accompanying drawings.

SUMMARY OF THE INVENTION

The dental implant of the present invention is defined by the claims with a specific embodiment shown in the attached drawings. For the purpose of summarizing the invention, the invention relates to a dental implant for placement into the jaw bone of the patient. The dental implant comprises a carrier body having a first end and a second end with a first aperture centrally positioned on the carrier body and extending from the first end and partially into the carrier body and a second aperture coaxially formed with the first aperture and extending through the carrier body. A foundation shaft having a first end and a second end is employed, with the first end of the foundation shaft terminating in a head having a diameter less than the diameter of the first aperture of the carrier body and greater than the diameter of the second aperture of the carrier body. The second end of the foundation shaft terminates in a jaw bone securing means for fixing the dental implant to the jaw bone of the patient. A supporting ring is secured proximate the first end of the foundation shaft and spaced apart relative to the second end of the carrier body. This head prevents, in use, axial movement of the carrier body along the foundation shaft in a first direction beyond the head and the supporting ring prevents axial movement of the carrier body along the foundation shaft in a second direction beyond the supporting ring thereby enabling axial movement of the carrier body along the foundation shaft between the second end of the carrier body and the supporting ring. The "first direction" is the direction toward the crown of the tooth and the "second direction" is the direction toward the jaw bone. An elongated body is employed having a first end and a second end, with the second end having an aperture formed therein. Preferably, the aperture is frustum shaped. That is, the volume of the aperture includes a frustum shape. A means is used for attaching in use an artificial tooth, or the like, at the first end of the elongated body. A connecting means secures the second end of the elongated body to the carrier body such that in use the attachment of the artificial tooth to the elongated body attached to the carrier body defines a tooth assembly. A resilient force dampening means is positioned into the aperture of the elongated body. The resilient force dampening means maintains contact of the carrier body with the head in the absence of masticatory movement of the jaw thereby maintaining the tooth assembly in a natural no-load appearance and resists axial movement of the tooth assembly in the second direction along the foundation shaft generated masticatory movement of the jaw thereby cushioning the masticatory forces received during use.

Preferably, the resilient force dampening means defines a resilient bi-frustum shaped body. However, other shapes which accomplish the purpose of the present invention are also envisioned, such as a circular shaped dampening means. The resilient force dampening means is preferably composed of silicon rubber. The preferred silicon rubber compositions are SILASTIC (HS 100U, HS 230U, HS 330U, most preferred; and LCS 140U, LCS 380U manufactured by Dow Corning Corp., U.S.A.), and TECH-SIL (HR-1130U, HR-1140U, HR-1150U, HR-1170U manufactured by HAE RYONG Silicone Co., Ltd., Korea). Other resilient compositions may be used. However, the composition of the resilient force dampening means should be oil resistant, physiologically inert, stable at high (hot foods) and low temperatures and flexible at low temperature (cold foods). Most preferably, the resilient force dampening means is composed of silicon rubber having a bi-frustum shape.

The bi-frustum shaped silicon rubber body, preferably, substantially fills the aperture formed in the elongated body and the silicon rubber body further includes an opening formed therethrough to permit a portion of the silicon rubber body to be received into the opening when the silicon rubber body is compressed, i.e. deformed, by the masticatory forces received during use.

The preferred means for attaching the artificial tooth at the first end of the elongated body includes a bore formed in the first end of the elongated body with internal threads to threadingly receive a bolt having external threads such that in use the bolt secures the artificial tooth to the elongated body.

The preferred connecting means for securing the second end of the elongated body to the carrier body is internal threads formed in the first aperture of the carrier body and external threads formed on the second end of the elongated body such that in use the external threads of the elongated body are threadingly received by the internal threads of the carrier body thereby securing the elongated body to the carrier body.

The axial movement of the carrier body along the foundation shaft between the second end of the carrier body and the supporting ring is preferably about 0.3 mm and most preferably 0.2 mm to accurately mimic the movement of a natural tooth.

The jaw bone securing means which secures the device of the present invention to the jaw of the patient. The jaw bone securing means includes blade form implants and sockets. Blade form implants are manufactured by Calcitek, Inc. (BIO BLADE) among others. The preferred jaw bone securing means is a dental socket, i.e. a cylinder shaped implant. Such sockets are well known in the art. For example, such sockets are manufactured by Core-vent Corporation (MICRO-VENT and BIO-VENT), Interpore International (INTERPORE IMZ) and Driskell Bioengineering among others.

Preferably, the dental implant for placement into a jaw comprises the combination of a carrier body with a first end and a second end and with a first aperture extending from the first end and partially into the carrier body and a second aperture coaxially formed with the first aperture and extending through the carrier body. A foundation shaft with a first end and a second end is used. The first end of the foundation shaft terminates in a head having a diameter less than the diameter of the first aperture of the carrier body and greater than the diameter of the second aperture of the carrier body. The second end of the foundation shaft terminates in the jaw bone securing means for fixing the dental implant to the jaw bone. A supporting ring is secured proximate the first end of the foundation shaft and is spaced apart relative to the second end of the carrier body. This structural assembly prevents axial movement of the carrier body along the foundation shaft in a first direction beyond the head and prevents axial movement of the carrier body along the foundation shaft in a second direction beyond the supporting ring thereby only allowing axial movement of the carrier body along the foundation shaft between the second end of the carrier body and the supporting ring. An elongated body with a first end and a second end is employed. The second end of the elongated body includes an aperture having a frustum shape formed therein. A means for attaching in use an artificial tooth at the first end of the elongated body is utilized. A connecting means secures the second end of the elongated body to the carrier body such that when the artificial tooth is attached to the elongated body, which in turn is attached to the carrier body, a tooth assembly is defined. A resilient force dampening means is positioned into the frustum shaped aperture of the elongated body. The resilient force dampening means maintains contact of the carrier body and the head in the absence of masticatory movement of the jaw thereby maintaining the tooth assembly in a natural no-load appearance. The resilient force dampening means also resists axial movement of the tooth assembly in the second direction along the foundation shaft generated masticatory movement of the jaw thereby cushioning the masticatory forces received during use.

The more pertinent and important features of the present invention have been outlined above in order that the detailed description of the invention which follows will be better understood and that the present contribution to the art can be fully appreciated. Additional features of the invention described hereinafter form the subject of the claims of the invention. Those skilled in the art can appreciate that the conception and the specific embodiment disclosed herein may be readily utilized as a basis for modifying or designing other structures for carrying out the same purposes of the present invention. Further, those skilled in the art can realize that such equivalent constructions do not depart from the spirit and scope of the invention as set forth in the claims.

BRIEF DESCRIPTION OF THE DRAWINGS

For a fuller understanding of the nature and objects of the invention, reference should be had to the following detailed description taken in connection with the accompanying drawings in which:

FIG. 1 is a sectional view of the dental implant of the present invention;

FIG. 2 is a plan view of the bi-frustum shaped body; and

FIG. 3 is a disassembled view of the dental implant of the present invention.

Similar reference characters refer to similar parts throughout the several views of the drawings.

DETAILED DESCRIPTION OF THE DRAWINGS

FIG. 1 illustrates the dental implant 10 according to the present invention fixed into the jaw bone 12.

The elongated body 50 has a first end 52 and a second end 54, with the second end having an aperture 56 formed therein. The aperture 56 of the elongated body, preferably, includes a frustum shape 58, as illustrated at FIG. 1.

The means 66 for attaching in use an artificial tooth 74 at the first end 52 of the elongated body 50 is utilized. The means 66 for attaching the artificial tooth 74 at the first end of the elongated body is preferably a bore 68, having internal threads 70, formed in the first end of the elongated body. A bolt 72 with external threads 73 engages the internal threads 70 of the bore 68 to threadably secure the artificial tooth, or the like, to the elongated body upon tightening the bolt 72 into the bore 68. Other dental prosthesis may be secured to the elongated body, such as a bridge, or the like, where natural tooth like action is desired.

The resilient force dampening means 90 is positioned in the aperture 56 formed in the elongated body 50. The resilient force dampening means acts as a spring. The resilient force dampening means 90 serves two functions. First, it maintains contact of the carrier body and the head in the absence of masticatory movement of the jaw, as shown at FIG. 1. That is, the tooth assembly is maintained in a natural no-load appearance. Second, it resists axial movement of the tooth assembly in the second direction along the foundation shaft thereby cushioning or attenuating the masticatory forces received by the foundation shaft during use. Such axial movement is generated during the masticatory movement of the jaw.

In the preferred embodiment the resilient force dampening means 90 is a resilient bi-frustum shaped body 92 composed of resilient silicon rubber 93 which is used in combination with a frustum shaped aperture 58 formed in the elongated body 50 and where the bi-frustum shaped body 92 composed of silicon rubber 93 substantially fills the frustum shaped aperture 58 formed in the elongated body. An opening 96 is formed through the silicon rubber body 93 which permits a portion of the silicon rubber body to be received into the opening in use when the silicon rubber body is compressed by the masticatory forces received during use. Preferably the opening 96 extends through the entire bi-frustum shaped body 92.

The carrier body 16 has a first end 18 and a second end 20 with a first aperture 22 extending from the first end, part way into the carrier body. The second aperture 24 is formed along the same axis as the first aperture 22 and coaxially extends from the bottom 25 of the first aperture completely through the carrier body. The diameter of the first aperture is greater than the diameter of the second aperture formed in the carrier body.

The foundation shaft 30 has a first end 32 and a second end 34 with the first end of the foundation shaft terminating in a head 36. The diameter 38 of the head is less than the diameter 26 of the first aperture 22 of the carrier body 16 and greater than the diameter 28 of the second aperture 24 of the carrier body. This prevents the carrier body 16 from moving along the foundation shaft and past the head 36. The diameter 39 of the foundation shaft 30 is slightly less than the diameter 28 of the second aperture 24 formed in the carrier body 16 to permit the passage of the foundation shaft 30 into the apertures 22, 24 of the carrier body 16. The second end 34 of the foundation shaft 30 terminates in a jaw bone securing means 40 which fixes the dental implant to the jaw bone. That is, the head and supporting ring limit the movement of the carrier body positioned between the head and the supporting ring to the distance between the head and the supporting ring less the length of the foundation shaft occupied by the carrier body.

The supporting ring 44 is secured, utilizing a press fit for example, proximate the first end 32 of the foundation shaft and spaced apart relative to the second end 20 of the carrier body 16. The head-supporting ring structural arrangement prevents axial movement of the carrier body along the foundation shaft 30 in a first direction 46 beyond the engagement of the bottom 25 of the first aperture 22 of the carrier body 16 by the head 36; and, also prevents axial movement of the carrier body along the foundation shaft in a second direction 48 beyond the supporting ring. The "first direction" 46 is the direction toward the crown of the tooth. Thus, the head 36 prevents the carrier body 16 from coming off the first end 32 of the foundation shaft 30. The "second direction" 48 is the direction toward the jaw bone. Thus, the supporting ring 44 prevents the carrier body 16 from bumping into the means which fixes the implant to the jaw, such as socket 42. In view of the spacing of the supporting ring and the head, the axial movement of the carrier body along the foundation shaft is limited to that length 49 of the foundation shaft which extends between the second end of the carrier body, i.e. the terminal end 17 of the carrier body, and the supporting ring 44. The axial movement of the carrier body along the foundation shaft between the second end of the carrier body and the supporting ring is, preferably, about 0.3 mm and most preferably 0.2 mm to mimic the movement and "feel" of a natural tooth.

The exact sizing of the supporting ring 44 and foundation shaft 30 will be determined by the relative size of the teeth of the patient being fitted with the dental implant according to the present invention in order to match the existing natural teeth. The connecting means 76 secures the elongated body to the carrier body. Upon attaching the artificial tooth 74 to the elongated body 50 which is itself attached to the carrier body 16 a tooth assembly 86 is defined. In practice the bolt securing the artificial tooth 74 to the elongated body 50 is covered by a white cement 75 to aid in simulating a natural looking tooth, to secure the bolt 72 in bore 68 and to protect the bolt 72 during chewing. Connecting means 76 secures the second end 54 of the elongated body 50 to the first end 18 of the carrier body 16. Preferably, the first aperture 22 formed in the carrier body includes internal threads 78 and the second end 54 of the elongated body 50 includes external threads 80. This enables the external threads 80 of the elongated body 50 to be threadingly received by the internal threads 78 of the carrier body 16 to secure the elongated body 50, including its attached artificial tooth, to the carrier body 16.

The vertical chewing forces are dampened by the resilient force dampening means. The lateral forces associated with chewing are dampened by the fit of the foundation shaft into the second aperture of the carrier body. That is, the tooth assembly 86 yields very slightly from the vertical plane to thereby dampen lateral force received by the tooth assembly.

FIG. 2 illustrates the bi-frustum shaped body 92 which has a first 92A and a second 92B frustum with a common base 95. The opening 96 preferably extends through the entire bi-frustum shaped body 92, i.e. from the first end 97 of the bi-frustum shaped body 92 thorough the second end 98 of the bi-frustum shaped body 92. In use, the opening 96 together with the peripheral void 99 between the frustum shaped aperture 58 and the bi-frustum shaped body 92 provides space for the bi-frustum shaped body 92 to be received during compression. That is, the bi-frustum shaped silicon rubber body substantially fills the frustum shaped aperture 58 formed in the elongated body 50. During use, the volume of the frustum shaped aperture of the elongated body is decreased by the intrusion of the head into the aperture caused by the chewing force exerted on the tooth assembly during chewing. The presence of the void 99 and the opening 96 permit a portion of the silicon rubber body to be received therein when the silicon rubber body is compressed during chewing. Because the volume of the void 99 is not enough for the silicon rubber body to deform into in the required quantity, the presence of the opening 96 in the bi-frustum body 92 is important. Thus, the volume of the void 99 and the opening 96 must be suitably designed in consideration of each other in order to provide space for the silicon rubber body to be deformed into in order to accomplish the required tooth assembly movement, i.e. the same as natural tooth movement.

Thus, the resilient silicon rubber body 93 having a bi-frustum shape 92 is received into an aperture 56 which includes a frustum shape 58. That is, the volume of the aperture includes a frustum shape. The frustum shaped 58 aperture 56 receives frustum 92A of the bi-frustum shaped body 92, while the remaining frustum 92B of the bi-frustum shaped body 92 is received into the volume below the frustum shaped 58 aperture 56, as illustrated at FIG. 1. Preferably, the resilient silicon rubber body 93 is bonded to the head 36 of the foundation shaft 30. The device 10 is symmetrical and displacement of the tooth assembly due to the load of the piston with respect to the resilient silicon rubber body 93 is along its axis of symmetry thereby mirroring natural tooth movement.

FIG. 3 illustrates the component parts of the dental implant of the present invention positioned for assembly of the device 10. A bolt 72 secures the artificial tooth, not shown, or other dental prosthesis to the elongated body 50. The connecting means 76 secures the elongated body 50 to the carrier body 16. The elongated body is then secured to the carrier body which enables the tooth assembly 86 to transfer the force received during chewing. When the device 10 is secured into the socket 42 and operatively positioned into the jaw of a patient, action simulating the movement of a natural tooth is made possible.

Although this invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention.

What is claimed is:

1. A dental implant for placement into a jaw bone, the dental implant comprising:
    a carrier body having a first end and a second end with a first aperture extending from said first end and partially into said carrier body and a second aperture coaxially formed with said first aperture and extending through said carrier body;
    a foundation shaft having a first end and a second end with said first end of said foundation shaft terminating in a head having a diameter less than the diameter of said first aperture of said carrier body and greater than the diameter of said second aperture of said carrier body and said second end of said foundation shaft terminating in a jaw bone securing means for fixing the dental implant to the jaw bone;
    a supporting ring secured proximate said first end of said foundation shaft and spaced apart relative to said second end of said carrier body such that in use said head prevents axial movement of said carrier body along said foundation shaft in a first direction beyond said head and said supporting ring prevents axial movement of said carrier body along said foundation shaft in a second direction beyond said supporting ring thereby enabling axial movement of said carrier body along said foundation shaft between said second end of said carrier body and said supporting ring;
    an elongated body having a first end and a second end, with said second end having an aperture formed therein;
    a means for attaching in use an artificial tooth at said first end of said elongated body;
    connecting means to secure said elongated body to said carrier body such that in use the attachment of said artificial tooth to said elongated body attached to said carrier body defines a tooth assembly; and
    a resilient force dampening means positioned in use into said aperture of said elongated body for maintaining contact of said carrier body and said head in the absence of masticatory movement of the jaw thereby maintaining said tooth assembly in a natural no-load appearance and for resisting axial movement of said tooth assembly in said second direction along said foundation shaft generated masticatory movement of the jaw thereby cushioning the masticatory forces received by said foundation shaft during use.

2. The dental implant of claim 1 wherein said aperture of said elongated body is frustum shaped.

3. The dental implant of claim 2 wherein said resilient force dampening means defines a bi-frustum shaped body.

4. The dental implant of claim 1 wherein said means for attaching in use an artificial tooth at said first end of said elongated body is a bore formed in said first end of said elongated body and having internal threads to receive a bolt having external threads secured to said artificial tooth such that in use said bolt threadingly secures said artificial tooth to said elongated body.

5. The dental implant of claim 1 wherein said connecting means to secure said second end of said elongated body to said carrier body wherein said first aperture formed in said carrier body includes internal threads and said second end of said elongated body includes external threads such that in use said external threads of said elongated are threadingly received by said internal threads of said carrier body thereby securing said elongated body to said carrier body.

6. The dental implant of claim 1 wherein said resilient force dampening means is a resilient silicon rubber body.

7. The dental implant of claim 1 wherein said resilient force dampening means is composed of silicon rubber having a bi-frustum shape.

8. The dental implant of claim 7 wherein said bi-frustum shaped silicon rubber body substantially fills said aperture formed in said elongated body.

9. The dental implant of claim 8 wherein said bi-frustum shaped silicon rubber body further includes an opening formed therethrough to permit a portion of said silicon rubber body to be received into said opening in use when said silicon rubber body is compressed by the masticatory forces received during use.

10. The dental implant of claim 1 wherein said axial movement of said carrier body along said foundation shaft between said head and said supporting ring is about 0.3 mm.

11. The dental implant of claim 1 wherein said jaw bone securing means is a dental socket.

12. A dental implant for placement into a jaw, the implant comprising:

a carrier body having a first end and a second end with a first aperture extending from said first end and partially into said carrier body and a second aperture coaxially formed with said first aperture and extending through said carrier body;

a foundation shaft having a first end and a second end with said first end of said foundation shaft terminating in a head having a diameter less than the diameter of said first aperture of said carrier body and greater than the diameter of said second aperture of said carrier body and said second end of said foundation shaft terminating in a jaw bone securing means for fixing the dental implant to the jaw bone;

a supporting ring secured proximate said first end of said foundation shaft and spaced apart relative to said second end of said carrier body such that in use said head prevents axial movement of said carrier body along said foundation shaft in a first direction beyond said head and said supporting ring prevents axial movement of said carrier body along said foundation shaft in a second direction beyond said supporting ring thereby enabling axial movement of said carrier body along said foundation shaft between said second end of said carrier body and said supporting ring;

an elongated body having a first end and a second end, with said second end having a frustum shaped aperture formed therein;

a means for attaching in use an artificial tooth at said first end of said elongated body;

connecting means to secure said elongated body to said carrier body such that in use the attachment of said artificial tooth to said elongated body attached to said carrier body defines a tooth assembly; and a resilient force dampening means comprising silicon rubber having a bi-frustum shape positioned in use into said frustum shaped aperture of said elongated body for maintaining contact of said carrier body and said head in the absence of masticatory movement of the jaw thereby maintaining said tooth assembly in a natural no-load appearance and for resisting axial movement of said tooth assembly in said second direction along said foundation shaft generated masticatory movement of the jaw thereby cushioning the masticatory forces received during use.

13. The dental implant of claim 12 wherein said bi-frustum shaped silicon rubber body substantially fills said frustum shaped aperture formed in said elongated body.

14. The dental implant of claim 13 wherein said bi-frustum shaped silicon rubber body further includes an opening formed therethrough to permit a portion of said silicon rubber body to be received into said opening in use when said silicon rubber body is compressed by the masticatory forces received during use.

* * * * *